(12) United States Patent
Bonitatibus, Jr. et al.

(10) Patent No.: US 8,246,932 B2
(45) Date of Patent: Aug. 21, 2012

(54) NON-RADIOACTIVE TRACEABLE METAL ISOTOPE-ENRICHED NANOPARTICLES AND METHOD OF THEIR USE FOR DETERMINING BIODISTRIBUTION

(75) Inventors: Peter John Bonitatibus, Jr., Saratoga Springs, NY (US); Amit Mohan Kulkarni, Clifton Park, NY (US); Andrew Soliz Torres, Troy, NY (US); Ying Zhou, Niskayuna, NY (US); Chiaki Treynor, Palo Alto, CA (US); Daniel Eugene Meyer, Rexford, NY (US)

(73) Assignee: General Electric Company, Niskayuna, NY (US)

( * ) Notice: Subject to any disclaimer, the term of this patent is extended or adjusted under 35 U.S.C. 154(b) by 1143 days.

(21) Appl. No.: 12/057,650

(22) Filed: Mar. 28, 2008

(65) Prior Publication Data

US 2009/0246143 A1    Oct. 1, 2009

(51) Int. Cl.
*A61B 5/055* (2006.01)
(52) U.S. Cl. ............. 424/9.34; 424/1.11; 424/1.61; 424/9.1; 424/9.2; 424/9.3
(58) Field of Classification Search .............. None
See application file for complete search history.

(56) References Cited

U.S. PATENT DOCUMENTS

| | | | |
|---|---|---|---|
| 5,427,767 | A | 6/1995 | Kresse et al. |
| 5,492,814 | A | 2/1996 | Weissleder |
| 6,797,380 | B2 | 9/2004 | Bonitatebus, Jr. et al. |
| 2006/0105052 | A1* | 5/2006 | Acar et al. .......... 424/490 |

FOREIGN PATENT DOCUMENTS

WO    2008/017944 A2    2/2008

OTHER PUBLICATIONS

Green. Chem Commun, 2005, 3002-3011.*
Ch. Aiexiou, Ch. Bergemann, R. Schmid, P. Hulin, A. Schmidt, R. Jurgons, W. Arnold, F. G. Parak; "Enrichment and Biodistribution of a Magnetically Targeted Drug Carrier"; European Cells and Materials vol. 3. Suppl. 2, 2002 (pp. 135-137).
Weissleder et al.; "Superparamagnetic Iron Oxide: Pharmacokinetics and Toxicity"; American Journal of Roentgenology, vol. 152, Issue 1, Jan. 1989; pp. 167-173.
R. Weissleder, G. Elizondo, J. Wittenberg, C.A. Rabito, H.H. Bengele and L. Josephson; "Ultrasmall Superparamagnetic Iron Oxide: Characterization of a New Class of Contrast Agents for MR Imaging"; Radiology, vol. 175, May 1990; pp. 489-493.
S. Majumdar, S. Zoghbi, C. F. Pope, J. C. Gore, ; "Quantitation of MR Relaxation Effects of Iron Oxide Particles in Liver and Spleen"; Radiology Dec. 1988; pp. 169: 653-655.
Brian Gulson and Herbert Wong; "Stable Isotopic Tracing—A Way Forward for Nanotechnology"; Environmental Health Perspectives, Oct. 2006; 114(10): 1486-1488.

* cited by examiner

*Primary Examiner* — Michael G Hartley
*Assistant Examiner* — Sean R Donohue
(74) *Attorney, Agent, or Firm* — Jenifer E. Haeckl

(57) ABSTRACT

Composition of non-radioactive traceable metal isotope-enriched nanoparticles, and methods of their use for determining in-vivo biodistribution are provided. The methods comprise the steps of: (a) introducing the nanoparticles into the biological material, wherein the nanoparticles comprise at least one inorganic core, and the inorganic core comprises at least two metal isotopes in a predetermined ratio; wherein at least one metal isotope is enriched non-radioactive traceable metal isotope and (b) determining the distribution of the nanoparticles in the biological material based on the predetermined ratio of the metal isotopes.

22 Claims, 3 Drawing Sheets

NON-RADIOACTIVE TRACEABLE METAL ISOTOPE-ENRICHED NANOPARTICLES AND METHOD OF THEIR USE FOR DETERMINING BIODISTRIBUTION

BACKGROUND

The invention relates generally to a composition of non-radioactive traceable metal isotope-enriched nanoparticles, and methods of their use for determining in-vivo biodistribution. One or more of the embodiments relate to non-radioactive traceable metal isotope-enriched superparamagnetic iron oxide (SPIO) nanoparticle composition and methods of their use for determining in-vivo biodistribution.

Superparamagnetic iron oxide (SPIO) nanoparticles of 10 to 1000 nm diameter are used as contrast agents to increase proton relaxation times in tissue following injection into patients to provide contrast enhancement in magnetic resonance imaging (MRI). It is often necessary to determine the nature of distribution of the contrast agent within the body. These determinations require detailed pharmacokinetic knowledge of the biodistribution and clearance of the contrast agent in animals, as well as blood and plasma clearance in human.

Although the degree of contrast observed by MRI depends upon the amount of contrast agent in a given tissue, it is generally not possible to quantitiatively determine the absolute concentration of conventional SPIO agents in a tissue. This is in part because of the effects of the SPIO agent on proton relaxation times. The SPIO agent's relaxivity properties may vary by interactions with proteins, cells or other components of the body and by possible metabolism or degradation of the SPIO agent within the body. Additionally, at lower concentrations of the SPIO agents, imaging sensitivity associated with MRI is a further barrier to quantitatively determine the concentration of the SPIO agents in tissue.

Other methods for determining SPIO concentrations in-vivo include iron-sensitive dyes, fluorescent/radioactive reporter labels, and quantitative elemental analysis. Qualitative methods, to determine SPIO distribution in tissue, rely on treating tissue specimens with iron staining agents, and cannot quantitatively determine biodistribution of the SPIO-based injected agents. Moreover, iron staining dyes do not necessarily distinguish between endogenous iron and SPIO nanoparticle associated iron. Dye, fluorophore, radioactive or other labels conjugated to the agent, change the composition of the SPIO particle, and may therefore alter its in-vivo performance. Furthermore, the label may not remain associated with the SPIO in-vivo, and thus tracking the label may not accurately reflect the distribution of the SPIO particle itself. In human studies, the potential risk of exposure to radioactive materials is also another concern. Elemental analysis of tissue samples to determine iron concentration could be achieved, however, with conventional SPIO agents, there is no way to distinguish between endogenous iron and SPIO-associated iron in the same tissue samples.

Therefore, there is a need for a label-free, non-radioactive method to quantitatively measure the in-vivo biodistribution of the injected nanoparticles such as SPIO nanoparticles.

BRIEF DESCRIPTION

The composition and methods of the invention are directed to the problem associated with radioactive nanoparticles at least in part by using non-radioactive traceable metal isotope-enriched nanoparticles. A "cold" or stable isotope with a low natural abundance is used herein, to facilitate tracking of the nanoparticle in-vivo. Moreover, one or more of the embodiments of the method are adapted to quantitate the nanoparticle biodistribution. For example, one embodiment of the method determines non-radioactive traceable metal isotope-enriched superparamagnetic iron oxide (SPIO) nanoparticle concentration in biological samples using elemental analysis. In one embodiment, Inductively Coupled Plasma Mass Spectroscopy (ICP-MS) may be used to determine the amount of non-radioactive traceable metal isotope-enriched nanoparticle (such as Iron (Fe) nanoparticle) distributed in organs. Isotopes such as $^{57}$Fe may be used as a suitable non-radioactive traceable metal isotope for biodistribution studies of the nanoparticles. However, it may often be required to enrich the nanoparticles with the suitable isotopes, especially when isotopes of lower natural abundance are used. In some embodiments, nanoparticles enriched with $^{57}$Fe may be provided to assay the biodistribution effectively.

One or more embodiments of the present invention comprise a non-radioactive traceable metal isotope-enriched nanoparticle composition. The nanoparticle comprises at least one inorganic core and at least one coating substantially covering the inorganic core. The inorganic core comprises at least one non-radioactive traceable metal isotope. The nanoparticle may have a diameter in a range of from about 1 nm to about 1000 nm. The coating may comprise a biocompatible material. The non-radioactive traceable metal isotope enrichment in the nanoparticle may be in a range of from about 1% to about 99%.

Another aspect of the present invention comprises a non-radioactive traceable metal isotope-enriched superparamagnetic nanoparticle. The superparamagnetic nanoparticle comprises at least one inorganic core and at least one coating substantially covering the inorganic core. The inorganic core comprises at least one non-radioactive traceable metal isotope. The inorganic core may comprise a superparamagnetic material. The superparamagnetic material may comprise a superparamagnetic iron oxide (SPIO). The non-radioactive traceable metal isotope may comprise $^{54}$Fe, $^{57}$Fe, $^{58}$Fe, or combinations thereof.

One or more of the embodiments describe methods of forming a plurality of non-radioactive traceable metal isotope-enriched nanoparticles. The method comprises the steps of: (a) combining a non-polar aprotic organic solvent, an oxidant, and a surfactant, to form a first solution; (b) adding at least one non-radioactive traceable metal isotope-enriched organometallic compound to the first solution, to form a second solution; and (c) heating the second solution to a temperature in a range of from about 30° C. to about 400° C., to form the plurality of nanoparticles. In one embodiment, each of the plurality of nanoparticles may be coated with a surfactant.

One or more embodiments provide one or more methods for determining the extent to which nanoparticles have been distributed within a biological material. One or more of these methods comprise the steps of: (a) introducing the nanoparticles into the biological material, and (b) determining the distribution of the nanoparticles in the biological material. The nanoparticles used herein comprise at least one inorganic core, wherein the inorganic core comprises at least two metal isotopes in a predetermined ratio, wherein at least one metal isotope is enriched non-radioactive traceable metal isotope. The distribution of the nanoparticles in the biological material may be determined by assaying the predetermined ratio of the metal isotopes present in the nanoparticles. The method may include elemental analysis to determine the distribution of the non-radioactive traceable metal isotopes.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
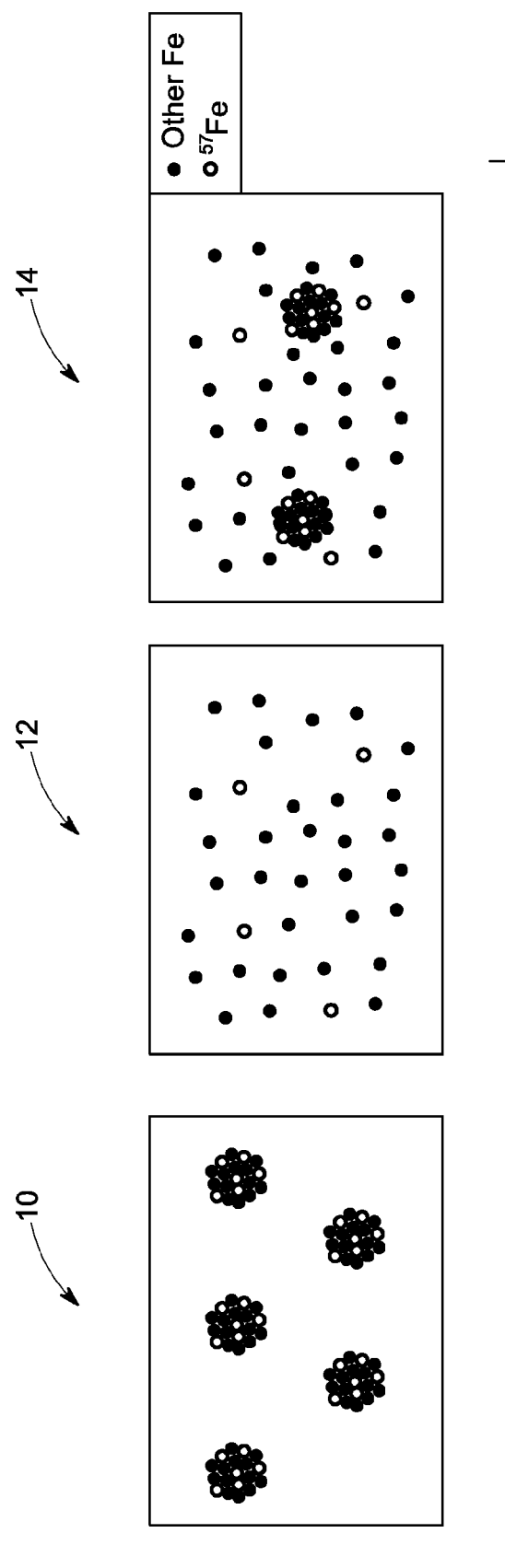
FIG. 1 shows a schematic representation of an embodiment of the non-radioactive traceable metal isotope-enriched nanoparticles of the invention.

The following detailed description is exemplary and not intended to limit the invention of the application and uses of the invention. Furthermore, there is no intention to be limited by any theory presented in the preceding background of the invention or the following detailed description.

In the following specification and the claims which follow, reference will be made to a number of terms have the following meanings. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Similarly, "free" may be used in combination with a term, and may include an insubstantial number, or trace amounts, while still being considered free of the modified term. For example, free of solvent or solvent-free, and like terms and phrases, may refer to an instance in which a significant portion, some, or all of the solvent has been removed from a solvated material.

One or more embodiments of the invention relate to composition of a nanoparticle. The nanoparticle comprises at least one inorganic core and at least one coating substantially covering the inorganic core. The inorganic core comprises at least one non-radioactive traceable metal isotope and the non-radioactive traceable metal isotope is enriched in the nanoparticle.

Nanoparticle as used herein refers to particles having an average particle size on the nano scale. A nanoparticle may have a largest dimension (for example, a diameter or length) in the range of from about 1 nm to about 1000 nm. In one embodiment, an average particle size of the nanoparticle may be in a range of less than about 1 nm. In one embodiment, an average particle size of the nanoparticle may be in a range of from about 1 nm to about 10 nm, from about 10 nm to about 25 nm, from about 25 nm to about 50 nm, from about 50 nm to about 75 nm, or from about 75 nm to about 100 nm.

As used herein, a nanoparticle may refer to a single particle or may include a plurality of particles. The plurality of particles may be characterized by one or more of average particle size, particle size distribution, average particle surface area, particle shape, or particle cross-sectional geometry.

A plurality of particles may have a distribution of particle sizes that may be characterized by both a number-average size and a weight-average particle size. The number-average particle size may be represented by $S_N = \Sigma(s_i n_i)/\Sigma n_i$, where $n_i$ is the number of particles having a particle size $s_i$. The weight average particle size may be represented by $S_W = \Sigma(s_i n_i^2)/\Sigma(s_i n_i)$. When all particles have the same size, $S_N$ and $S_W$ may be equal. In one embodiment, there may be a distribution of sizes, and $S_N$ may be different from $S_W$. The ratio of the weight average to the number average may be defined as the polydispersity index ($S_{PDI}$). In one embodiment, $S_{PDI}$ may be equal to about 1. In one embodiment, $S_{PDI}$ may be in a range of from about 1 to about 1.2, from about 1.2 to about 1.4, from about 1.4 to about 1.6, or from about 1.6 to about 2.0. In one embodiment, $S_{PDI}$ may be in a range that is greater than about 2.0.

In one embodiment, the metal nanoparticle may include a plurality of particles having a particle size distribution selected from a group consisting of normal distribution, unimodal distribution, and bimodal distribution. Certain particle size distributions may be useful to provide certain benefits, and other ranges of particle size distributions may be useful to provide other benefits. A normal distribution may refer to a distribution of particle sizes with $S_{PDI}$ equal to 1. A unimodal distribution may refer to a distribution of particle sizes having the same particle size. In another embodiment, particles having two distinct size ranges (a bimodal distribution) may be included in the composition: the first range from about 1 nm to about 10 nm and the second range from about 20 nm to about 50 nm.

A nanoparticle may have a variety of shapes and cross-sectional geometries that may depend, in part, upon the process used to produce the particles. In one embodiment, a nanoparticle may have a shape that is a sphere, a rod, a tube, a flake, a fiber, a plate, a wire, a cube, or a whisker. A nanoparticle may include particles having two or more of the aforementioned shapes. In one embodiment, a cross-sectional geometry of the particle may be one or more of circular, ellipsoidal, triangular, rectangular, or polygonal. In one embodiment, a nanoparticle may consist essentially of non-spherical particles. For example, such particles may have the form of ellipsoids, which may have all three principal axes of differing lengths, or may be oblate or prelate ellipsoids of revolution. Non-spherical nanoparticles may alternatively be laminar in form, wherein laminar refers to particles in which the maximum dimension along one axis is substantially less than the maximum dimension along each of the other two axes. Such laminar nanoparticles may have a shape similar to the tabular silver halide. Non-spherical nanoparticles may also have the shape of frusta of pyramids or cones, or of elongated rods. In one embodiment, the nanoparticles may be irregular in shape. In one embodiment, the nanoparticle may consist essentially of spherical particles.

A nanoparticle may have a high surface-to-volume ratio. A nanoparticle may be crystalline or amorphous. In one embodiment, a single type (size, shape, and the like) of nanoparticle may be used, or mixtures of different types of nanoparticles may be used. If a mixture of nanoparticles is used they may be homogeneously or non-homogeneously distributed in the composition.

In one embodiment, the metal nanoparticle may be stable towards aggregate or agglomerate formation. An aggregate may include more than one nanoparticle in physical contact with one another, while agglomerates may include more than one aggregate in physical contact with one another. In some embodiments, the nanoparticles may not be strongly agglomerated and/or aggregated such that the particles may be relatively easily dispersed in the composition.

In one or more embodiments, the nanoparticles comprise at least one inorganic core, wherein the inorganic core comprises at least one natural metal isotope and at least one non-radioactive traceable metal isotope, and the non-radioactive traceable metal isotope is enriched in the nanoparticle.

As used herein, the term "natural metal isotope" refers to a stable metal isotope that is present in the nanoparticle in its naturally occurring state and is non-enriched. As an example, the different isotopes of iron have a natural abundance of $^{54}$Fe (5.84%), $^{56}$Fe (91.7%), $^{57}$Fe (2.11%) and $^{58}$Fe (0.28%). Accordingly, for a nanoparticle enriched with $^{57}$Fe, the natural metal isotope may include $^{54}$Fe, $^{56}$Fe, or $^{58}$Fe. In some embodiments, the abundance of the natural metal isotope may be used to determine the distribution of the nanoparticle in the biological material, and accordingly the natural metal isotope may be chosen such that its concentration may be determined by an elemental analysis technique.

In one embodiment, the inorganic core comprises at least one natural metal isotope of a metal selected from a group consisting of iron, manganese, copper, titanium, cadmium, cobalt, nickel, chromium, gadolinium, yttrium, zinc, molybdenum, vanadium, and derivatives thereof.

In one embodiment, the natural metal isotope may comprise of isotopes of transition metals, lanthanides, or combinations thereof. In one embodiment, the natural metal isotope comprises an isotope of at least one metal selected from a group consisting of iron, manganese, copper, titanium, cadmium, cobalt, nickel, chromium, gadolinium, yttrium, zinc, molybdenum, vanadium, and combinations thereof. In one embodiment, an inorganic core comprises a compound of a natural metal isotope. Suitable compounds may comprise of oxides, nitrides, carbides, sulfides, phosphides, selenides, tellurides, borides, or combinations thereof. In some embodiments, a natural metal isotope may include $^{54}$Fe or $^{56}$Fe.

As used herein, the term "non-radioactive traceable metal isotope" refers to a metal isotope that may be a cold or a stable isotope. A non-radioactive traceable metal isotope present in the nanoparticle is enriched. As used herein, the term "enriched non-radioactive traceable metal isotope" refers to a non-radioactive traceable metal isotope present in the nanoparticle at an abundance that is greater than its natural abundance. In one embodiment, the abundance of the non-radioactive traceable metal isotope in the nanoparticle may be characterized by its enrichment value. As used herein, the term "non-radioactive traceable metal isotope enrichment" refers to the relative percentage of the number of the non-radioactive traceable metal isotopes present in the nanoparticle compared to the total number of metal isotopes present in the nanoparticle. Thus, by way of example, a nanoparticle comprising an enriched $^{57}$Fe isotope comprises $^{57}$Fe in an abundance that is greater than 2.11%. Similarly, a nanoparticle comprising an enriched $^{54}$Fe isotope comprises $^{54}$Fe in an abundance that is greater than 5.84%.

In one embodiment, the non-radioactive traceable metal isotope enrichment may be in a range of from about 1% to about 99%. In another embodiment, the non-radioactive traceable metal isotope enrichment may be in a range of from about 2% to about 99%, from about 5% to about 80%, from about 10% to about 70%, or from about 20% to about 50%. In some embodiments, the nanoparticle may be enriched with at least about 10% non-radioactive traceable metal isotope. In other embodiments, the nanoparticle may be enriched with at least about 20% non-radioactive traceable metal isotope. In other embodiments, the nanoparticle may be enriched with at least about 50% non-radioactive traceable metal isotope. In other embodiments, the nanoparticle may be enriched with at least about 90% non-radioactive traceable metal isotope. In one embodiment, the non-radioactive traceable metal isotope enrichment in the nanoparticle may be in a range of from about 10% to about 20%.

In one embodiment, the non-radioactive traceable metal isotopes may comprise an isotope of transition metals, lanthanides, or combinations thereof. In one embodiment, the non-radioactive traceable metal isotope comprises an isotope of at least one metal selected from a group consisting of iron, manganese, copper, titanium, cadmium, cobalt, nickel, chromium, gadolinium, yttrium, zinc, molybdenum, and vanadium, and combinations thereof. In one embodiment, an inorganic core comprises a compound of a non-radioactive traceable metal isotope. Suitable compounds may comprise of oxides, nitrides, carbides, sulfides, phosphides, selenides, tellurides, borides, or combinations thereof. In some embodiments, the non-radioactive traceable metal isotope may include $^{54}$Fe, $^{57}$Fe, or $^{58}$Fe.

In some embodiments, the inorganic core comprises a single enriched non-radioactive traceable metal isotope. In another embodiment, the inorganic core comprises two or more enriched non-radioactive traceable metal isotopes. In embodiments, where the inorganic core comprises two or more enriched non-radioactive traceable metal isotopes, the enriched non-radioactive traceable metal isotopes may be of the same metal or of two or more different metals. For example, in one embodiment, the enriched non-radioactive traceable metal isotope may comprise of different isotopes of a single metal, for example isotopes of $^{54}$Fe, $^{57}$Fe, $^{58}$Fe or combinations thereof. In another embodiment, the enriched non-radioactive traceable metal isotope may comprise two or more different transition metals, for example different isotopes of Fe and Mn. In another embodiment, the enriched non-radioactive traceable metal isotope may be comprised of two or more different lanthanides, for example isotopes of Gd and Yb. In another embodiment, the enriched non-radioactive traceable metal isotope may be comprised of different isotopes of transition metals and lanthanides, for example isotopes of Fe and Gd.

In some embodiments, the non-radioactive traceable metal isotope may comprise a non-radioactive traceable iron isotope. In one embodiment, the non-radioactive traceable iron isotope comprises $^{54}$Fe, $^{57}$Fe, $^{58}$Fe or combinations thereof Depending on the iron isotope employed, the iron isotope may be suitably enriched in the nanoparticle. In some embodiments, the non-radioactive traceable iron isotope enrichment in the nanoparticle may be in a range of from about 1% to about 99%. In some embodiments, the nanoparticle may be enriched with at least about 10% non-radioactive traceable iron isotope. In other embodiments, the nanoparticle may be enriched with at least about 20% non-radioactive traceable iron isotopes. In other embodiments, the nanoparticle may be enriched with at least about 50% non-radioactive traceable iron isotopes. In some embodiments, the nanoparticle may be enriched with at least about 90% non-radioactive traceable iron isotopes. In one embodiment, the non-radioactive traceable iron isotope enrichment in the nanoparticle may be in a range of from about 10% to about 20%. In some embodiments, the non-radioactive traceable metal isotope may include $^{57}$Fe. In embodiments including $^{57}$Fe as non-radioactive traceable metal isotope, the enrichment of $^{57}$Fe in the nanoparticle may be in a range that is greater than 2.5%.

In one embodiment, the inorganic core may be covered with at least one coating substantially covering the core. In one embodiment, the coating may serve to stabilize the inorganic core, i.e., the coating may prevent one inorganic core from contacting an adjacent inorganic core, thereby preventing a plurality of such nanoparticles from aggregating or agglomerating as described herein. In one embodiment, the coating may be of a sufficient thickness to stabilize the inorganic core and prevent such contact. In one embodiment, the coating has a thickness in a range of from about 1 nm to about 50 nm. In another embodiment, the coating has a thickness in a range of from about 1.5 nm to about 3 nm.

As used herein, the term "substantially covering" means that a percentage surface coverage of the nanoparticle is in a range that is greater than about 20%. Percentage surface coverage refers to the ratio of nanoparticle surface covered by the coating to the surface area not covered by the coating. In some embodiments, the percentage surface coverage of the nanoparticle may be in a range of from about 20% to about 80%. In other embodiments, the percentage surface coverage of the nanoparticle may be in a range of from about 40% to about 60%. In another embodiment, the percentage surface coverage of the nanoparticle is in a range that is greater than about 90%.

The inorganic core may be covered with one or more coating. In embodiments, where the inorganic core may be covered with more than one coating, the coating may be of the same or of different material. In embodiments, where more than one coating is present, the biocompatible material may be used for at least one coating. In some embodiments, all the coatings may be biocompatible. The non-limiting examples of a biocompatible coating include organo-silane compounds, polyketal polymers, dextran, poly (L) lactic acid, polycaprolactone, polyurethane, or combinations thereof. In some embodiments, a biocompatible coating may include organo-silane compounds. In some embodiments, the organo-silane compounds may be further derivatized with polyethylene glycol (PEG), polyethylene imine (PEI), dextran, or combinations thereof.

In some embodiments, the coating may further comprise of a spacer. In one embodiment, the spacer may comprise of alkyl groups, aryl groups, substituted alkyl and aryl groups, heteroalkyl (e.g., oxo groups, alkyl amine group), or heteroaryl groups. In some embodiments, the spacer may comprise of p-aminobenzyl, substituted p-aminobenzyl, diphenyl, substituted diphenyl, alkyl furan (e.g, benzylfuran), carboxy, or straight chain alkyl groups of 1 to 10 carbons in length. In some particular embodiments, the spacer may comprise of p-amino benzyl, methyl, ethyl, propyl, butyl, pentyl, hexyl, acetic acid, propionic acid, amino butyl, p-alkyl phenols, 4-alkylimidazole, carbonyls, OH, COOH, or glycols.

In some embodiments, the coating "substantially covering" the core may facilitate one or more of improved water solubility, reduces aggregate formation, reduces agglomerate formation, prevent oxidation of nanoparticles, maintain uniform core-shell entity, or biocompatibility of the nanoparticles. In another embodiment, the material or materials comprising the coating may later be replaced or functionalized by other materials that are tailored for a particular application, such as, but not limited to, diagnostic application.

In one embodiment, the nanoparticle may further be functionalized with a targeting moiety. The targeting moiety may be a molecule or a structure that provides targeting of the nanoparticle to desired organs, tissues or cells. The targeting moiety may include, but is not limited to, proteins, peptides, antibodies, nucleic acids, sugar derivatives, or combinations thereof.

In some embodiments, the nanoparticle may comprise a single inorganic core. In some embodiments, the nanoparticle may comprise a plurality of inorganic cores. In embodiments comprising plurality of inorganic cores, at least one inorganic core comprises an enriched non-radioactive traceable metal isotope. In some embodiments, at least two inorganic cores comprise an enriched non-radioactive traceable metal isotope. In other embodiments, each of the inorganic cores comprises an enriched non-radioactive traceable metal isotope. In some embodiments, at least one of the inorganic cores may not contain any non-radioactive traceable metal isotope.

In embodiments involving plurality of inorganic cores having an enriched non-radioactive traceable metal isotope, the non-radioactive traceable metal isotope may be of the same or of different metal in the different inorganic cores. In one exemplary embodiment, both a first and a second inorganic core may be enriched with $^{57}$Fe. In another exemplary embodiment, a first inorganic core may be enriched with $^{54}$Fe and a second inorganic core may be enriched with $^{57}$Fe. In another exemplary embodiment, a first inorganic core may be enriched with a non-radioactive traceable metal isotope of Fe and a second inorganic core may be enriched with a non-radioactive traceable metal isotope of Mn.

The inorganic cores may be covered with one or more coatings. In some embodiments, the plurality of inorganic cores may be covered with the same coating. In one embodiment, a single coating may cover all the inorganic cores present in the nanoparticle. In some embodiments, the individual cores may further be covered with one or more coatings. In another embodiment, all the inorganic cores present in the nanoparticle may be covered with two or more coatings. The individual coating may comprise the same material or may comprise two or more different materials.

In one or more embodiments, the present invention relates to a composition of a superparamagnetic nanoparticle. "The superparamagnetic nanoparticle" as used herein refers to nanoparticles that may exhibit a behavior similar to paramagnetism even when at temperatures below the Curie or the Néel temperature.

In some embodiments, the superparamagnetic nanoparticle composition comprises at least one inorganic core and at least one coating substantially covering the inorganic core. The inorganic core comprises at least one non-radioactive traceable metal isotope and the non-radioactive traceable metal isotope is enriched in the nanoparticle. In some embodiments, the inorganic core comprises a superparamagnetic material.

In some embodiments, the superparamagnetic nanoparticle comprises at least one natural metal isotope, and at least one non-radioactive traceable metal isotope in a predetermined ratio. In other embodiments, the superparamagnetic nanoparticle comprises at least one superparamagnetic iron oxide (SPIO) core. The SPIO core comprises a non-radioactive traceable metal isotope. In some embodiments, the non-radioactive traceable metal isotope in the SPIO core may comprise at least one isotope of iron, for example, $^{54}$Fe, $^{57}$Fe, or $^{58}$Fe. In other embodiments, the non-radioactive traceable metal isotope in the SPIO core may comprise at least one non-iron isotope, for example, a non-radioactive traceable isotope of Mn. In some embodiments, the SPIO core may include enriched non-radioactive traceable metal isotope. The non-radioactive traceable metal isotope enrichment may be in a range of from about 2% to about 99%. In some embodiments, the non-radioactive traceable metal isotope enrichment may be in a range of from about 60% to about 90%. In some other embodiments, the non-radioactive traceable metal isotope enrichment may be in a range of from about 10% to about 25%. In some embodiments, the non-radioactive traceable metal isotope may be $^{54}$Fe, $^{57}$Fe, or $^{58}$Fe.

In some embodiments, the superparamagnetic nanoparticle may have a diameter in a range of from about 1 nm to about 1000 nm. In one or more of the embodiments, the nanoparticle may have a diameter in a range of from about 1 nm to about 100 nm. In other embodiments, the nanoparticle may have a diameter in a range of from about 1 nm to about 10 nm.

In some embodiments, the superparamagnetic nanoparticle comprises a single SPIO core. The SPIO core may have one or more coating substantially covering the SPIO core. In embodiments, where more than one coating is present, the coating may be of the same material or of different materials. In some embodiments, the superparamagnetic nanoparticle comprises a single SPIO core and at least one additional core. In some embodiments, the superparamagnetic nanoparticle comprises one or more inorganic cores in addition to one or more SPIO cores.

In some embodiments, the superparamagnetic nanoparticle comprises a plurality of SPIO cores. The plurality of SPIO cores may have one or more coatings substantially covering the SPIO cores. In embodiments, where more than one coating is present, the coating may be of the same material or of different materials. In some embodiments, two or more of the SPIO cores may be covered with one and the same coating. In some embodiments, the individual cores may further be covered with one or more additional coatings. In some embodiments, some of the superparamagnetic iron oxide (SPIO) cores may not contain non-radioactive traceable metal isotopes. In some embodiments, each of the SPIO cores may comprise at least one non-radioactive traceable metal isotope.

In some embodiments, the nanoparticles of the present invention may be used as magnetic resonance (MR) contrast agents. These nanoparticles may yield a T2*, T2, or T1 magnetic resonance signal upon exposure to a magnetic field.

Another aspect of the invention is to provide a method for making a plurality of nanoparticles. The method comprises the steps of (a) combining a non-polar aprotic organic solvent, an oxidant, and a surfactant, to form a first solution, (b) adding at least one organometallic compound to the first solution, to form a second solution, and (c) heating the second solution to a temperature in a range from about 30° C. to about 400° C., to form the plurality of nanoparticles. The plurality of nanoparticles comprises at least one inorganic core derived from the organometallic compound. The inorganic core comprises at least one non-radioactive traceable metal isotope. The plurality of nanoparticles further comprises at least one coating derived from the surfactant.

In one embodiment, the non-polar aprotic organic solvent may be thermally stable at the temperature at which the plurality of nanoparticles is formed. In one embodiment, the non-polar aprotic solvent has a boiling point in a range of from about 275° C. to about 340° C. Suitable non-polar aprotic solvents include, but are not limited to, dioctyl ether, hexadecane, trioctylamine, tetrathylene glycol dimethyl ether (also known as "tetraglyme"), or combinations thereof.

In one embodiment, the oxidant comprises at least one organo-tertiary amine oxide, a peroxide, an alkyl hydroperoxide, a peroxy-acid, molecular oxygens, nitrous oxide, or combinations thereof. In one embodiment, the oxidant comprises an organo-tertiary amine oxide having at least one methyl group. One non-limiting example of such an oxidant is trimethyl amine oxide.

In one embodiment, the surfactant comprises a polymerizable functionalized group, an initiating functionalized group, a cross-linking functionalized group, or combinations thereof. In one embodiment, the polymerizable functionalized group may comprise at least one of an alkene, an alkyne, a vinyl (including acrylics and styrenics), an epoxide, an azeridine, a cyclic ether, a cyclic ester, a cyclic amide, or combinations thereof. In one embodiment, the initiating functionalized group may comprise at least one of a thermal or a photoinitiator, such as, but not limited to, an azo compound, a hydroxide, a peroxide, an alkyl halide, an aryl halide, a halo ketone, a halo ester, a halo amide, a nitroxide, a thiocarbonyl, a thiol, an organo-cobalt compound, a ketone, an amine, or combinations thereof. In one embodiment, the cross-linking functionalized group may comprise at least one of a thiol, an aldehyde, a ketone, a hydroxide, an isocyanide, an alkyl halide, a carboxylate, a carboxylic acid, a phenol, an amine, or combinations thereof.

In one embodiment, the at least one organometallic compound comprises at least one non-radioactive traceable metal isotope and at least one ligand. In one embodiment, the organometallic compound comprises a non-radioactive traceable metal isotope of a transition metal, a lanthanide, or combinations thereof. In another embodiment, the organometallic compound comprises a non-radioactive traceable metal isotope of at least one metal selected from a group consisting of iron, manganese, copper, titanium, cadmium, cobalt, nickel, chromium, gadolinium, yttrium, zinc, molybdenum, vanadium, and combinations thereof.

A suitable ligand may comprise, but is not limited to, a carbonyl group, a cyclo octadienyl group, an organophosphine group, a nitrosyl group, a cyclo pentadienyl group, a pentamethyl cyclo pentadienyl group, a [π]-acid ligand, a nitroxy group, or combinations thereof. Non-limiting examples of the organometallic compound include iron carbonyl ($Fe(CO)_5$), cobalt carbonyl ($Co(CO)_8$), or manganese carbonyl ($Mn_2(CO)_{10}$). In one embodiment, an amount of the organometallic compound may be introduced into the aprotic solvent such that a ratio of the concentration of the organometallic compound to the concentration of the oxidant is from about 1:1 to about 10:1.

In one embodiment, the second solution may be heated to a first temperature for first time interval. The first temperature may be in a range of from about 50° C. to about 400° C. In one embodiment, the first temperature is in a range of from about 275° C. to about 400° C. and preferably, in a range of from about 275° C. to about 310° C. The length of the first time interval may be in a range of from about 30 minutes to about 2 hours, depending on the particular organometallic compounds and oxidants that are in the aprotic solvent. One skilled in the art, given the benefit of this disclosure will be able to derive appropriate temperature and time interval that are suitable for synthesizing the plurality of nanoparticles.

In one embodiment, the method may further comprise the step of: precipitating the plurality of nanoparticles from the non-polar aprotic solvent. Precipitation of the plurality of nanoparticles may be accomplished by adding at least one of an alcohol or a ketone to the non-polar aprotic solvent. Alcohols such as, but not limited to, methanol and ethanol may be used. Alcohols having at least three carbon atoms, such as isopropanol, are preferred. Ketones such as, but not limited to, acetone may be used in conjunction with, or separate from, an alcohol in the precipitation step.

In one embodiment, the method further comprises reacting or interacting the metal nanoparticles with a biocompatible material to form a biocompatible coating of the nanoparticle. In one embodiment, the biocompatible material either partially or completely replaces or is exchanged with the surfactant in the coating. Following the formation of the plurality of nanoparticles, the biocompatible material may be added to the nonpolar aprotic solvent such that the biocompatible material is present in a concentration, greater than the concentration of the surfactant in the nonpolar aprotic solvent. Non-limiting examples of biocompatible materials include organo-silane compounds, polyketal polymers, dextran, poly (L) lactic acid, polycaprolactone, polyurethane, or combinations thereof. In some embodiments, the biocompatible material may include organo-silane compounds. In some embodiments, the organo-silane compounds may be further derivatized with polyethylene glycol (PEG), polyethylene imine (PEI), dextran, or combinations thereof.

One embodiment of the invention describes the method for determination of the extent to which the nanoparticles are distributed within a biological material. The nanoparticles may be introduced to the biological material by a variety of known methods. Non-limiting examples for introducing the nanoparticle to the biological material include intravenous administration, oral, dermal application, or direct injection into muscle, skin, the peritoneal cavity or other tissues or bodily compartments. The method comprises the steps of: (a) introducing the nanoparticles into the biological material, wherein the nanoparticles comprise at least one inorganic core, and the inorganic core comprises at least two metal isotopes in a predetermined ratio, wherein at least one metal isotope is enriched non-radioactive traceable metal isotope, and (b) determining the distribution of the nanoparticles in the biological material based on the predetermined ratio of the metal isotopes.

As used herein, the term "predetermined ratio" refers to a ratio of the abundance of the two metal isotopes in the nanoparticle. In one embodiment, at least one metal isotope is a non-radioactive traceable metal isotope. In another embodiment, both the metal isotopes are non-radioactive traceable metal isotopes. As described herein above, the non-radioactive traceable metal isotope may be enriched in the nanoparticle. In another embodiment, one of the metal isotope is a natural metal isotope, which is non-enriched. Thus, in one embodiment, the predetermined ratio is the ratio of the abundance of the two enriched non-radioactive traceable metal isotopes. In another embodiment, the predetermined ratio is the ratio of the abundance of the enriched non-radioactive traceable metal isotope to the natural abundance of the natural metal isotope in the nanoparticle.

Another embodiment, of the invention describes the method for determination of the extent to which the superparamagnetic nanoparticles may be distributed within a biological material. The method comprises the steps of (a) introducing the superparamagnetic nanoparticles into the biological material, where the superparamagnetic nanoparticles comprise at least one superparamagnetic core, wherein the superparamagnetic core comprises at least two metal isotopes in a predetermined ratio; wherein at least one metal isotope is enriched non-radioactive traceable metal isotope, and (b) determining the distribution of the superparamagnetic nanoparticles in the biological material based on the predetermined ratio of the metal isotopes.

In another embodiment, the distribution of the nanoparticle comprising non-radioactive traceable metal isotopes in the biological material may be determined by elemental analysis. In one embodiment, Inductively Coupled Plasma Mass Spectroscopy (ICP-MS) may be used to determine the concentration of the nanoparticles in the biological material.

In one embodiment, the predetermined ratio may be related to the distribution of nanoparticle in the biological material. In one embodiment, the distribution of nanoparticle in the biological material may be determined by measuring the ratio of two non-radioactive traceable metal isotopes present in the biological material. In another embodiment, the distribution of nanoparticle in the biological material may be determined by measuring the ratio of non-radioactive traceable metal isotope and natural metal isotope present in the biological material. The amount of natural metal isotope present in the biological material is the sum of the natural metal isotope present in the nanoparticle and the natural metal isotope already present in the biological material at its natural abundance. The amount of non-radioactive traceable metal isotope present in the biological material is sum of the enriched non-radioactive traceable metal isotope present in the nanoparticle and the non-radioactive traceable metal isotope already present in the biological material at its natural abundance.

In one exemplary embodiment, $^{57}$Fe-enriched SPIO nanoparticle ($^{57}$Fe$_{SPIO}$) may be employed to determine $^{57}$Fe$_{SPIO}$ concentration in biological samples for characterization of biodistribution and clearance of the nanoparticle. As described herein, 3 isotopic ratios of $^{57}$Fe to $^{54}$Fe may be employed to determine distribution of SPIO in the biological sample. One of the three ratios is the ratio of non-radioactive traceable iron isotopes ($^{57}$Fe$_{SPIO}$ to $^{54}$Fe$_{SPIO}$) in the superparamagnetic iron oxide ($^{57}$Fe$_{SPIO}$) nanoparticle—(represented by 'S'). The ratio of non-radioactive traceable iron isotopes ($^{57}$Fe$_{SPIO}$ to $^{54}$Fe$_{SPIO}$) may be measured by elemental analysis for each of the $^{57}$Fe$_{SPIO}$. Second of the three ratios is the ratio of natural abundance of the $^{57}$Fe$_{natural}$ to $^{54}$Fe$_{natural}$ in a tissue sample (represented by 'N'). The third ratio is the ratio of the non-radioactive traceable iron isotopes ($^{57}$Fe$_{sample}$ to $^{54}$Fe$_{sample}$) (represented by 'M') measured in a biological sample by elemental analysis upon the biological sample being injected with $^{57}$Fe$_{SPIO}$.

As described hereinabove, M depends on both on the endogenous iron content of the tissue and on the concentration of $^{57}$Fe-enriched SPIO in the tissue. M may be represented by:

$$M = \frac{^{57}Fe_{sample}}{^{54}Fe_{sample}}$$
$$= \frac{^{57}Fe_{SPIO} + ^{57}Fe_{natural}}{^{54}Fe_{SPIO} + ^{54}Fe_{natural}}$$

The concentration of $^{57}$Fe in the sample attributable to $^{57}$Fe$_{SPIO}$ may be then calculated as:

$$^{57}Fe_{SPIO} = \frac{^{57}Fe_{sample}/M - ^{57}Fe_{sample}/N}{1/S - 1/N}$$

Based on the $^{57}$Fe enrichment in the $^{57}$Fe$_{SPIO}$ preparation (e.g., $^{57}$Fe$_{SPIO}$: SPIO (SPIO with no enrichment), the total iron concentration in the tissue attributable to $^{57}$Fe$_{SPIO}$ may be calculated by:

SPIO distributed in the biological material=$^{57}$Fe$_{SPIO}$/Enrichment

EXAMPLES

Practice of the invention will be still more fully understood from the following examples, which are presented herein for illustration only and should not be construed as limiting the invention in any way.

The abbreviations used in the examples section are expanded as follows: "mg": milligrams; "mL": milliliters; "mg/mL": milligrams per milliliter; "mmol": millimoles; "μL" and μLs: microliters; "ICP-MS": Inductively Coupled Plasma Mass Spectroscopy; "MALDI-MS": Matrix Assisted Laser Desorption Ionization Mass Spectrometry; "HPLC":

High Pressure Liquid Chromatography; ppb: parts per billion; "TEM": Transmission Electron Microscopy; "EDX": Energy Dispersive X-ray Elemental Analysis, "XAS": X-ray Absorption Spectroscopy; "SAED-XRD": Selected Area Electron Diffraction-X-ray Diffraction Crystal Symmetry pattern Indexing.

Unless otherwise noted, all reagent-grade chemicals were used as received, and Millipore water was used in the preparation of all aqueous solutions. The $^{57}$Fe was purchased from Cambridge Isotope Laboratories, Inc. Andover Mass., as iron-57 oxide ($^{57}$Fe>95% enrichment).

Example 1

Synthesis of $^{57}$Fe (CO)$_5$

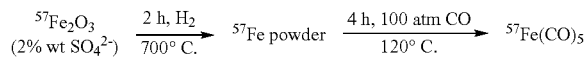

Iron-57 oxide ($^{57}$Fe$_2$O$_3$) was converted to non-radioactive isotopically enriched iron-57 metal ($^{57}$Fe) by heating the Iron-57 oxide at 700° C. under H$_2$ atmosphere for 2 h. In a subsequent step, the iron-57 metal ($^{57}$Fe) was subjected to carbonylation reaction at around 120° C. for at least 4 hours, under at least 100 atmospheric carbon monoxide (CO) pressure to obtain non-radioactive isotopically enriched iron-57 carbonyl ($^{57}$Fe(CO)$_5$). Typically, the $^{57}$Fe$_2$O$_3$ was combined with a larger portion of commercially available (regular) Fe$_2$O$_3$ for ease in materials handling to prepare $^{57}$Fe-enriched Fe(CO)$_5$. The %-enrichment of Fe(CO)$_5$ is then determined by the ratio of $^{57}$Fe$_2$O$_3$/Fe$_2$O$_3$ used.

Figure 2:
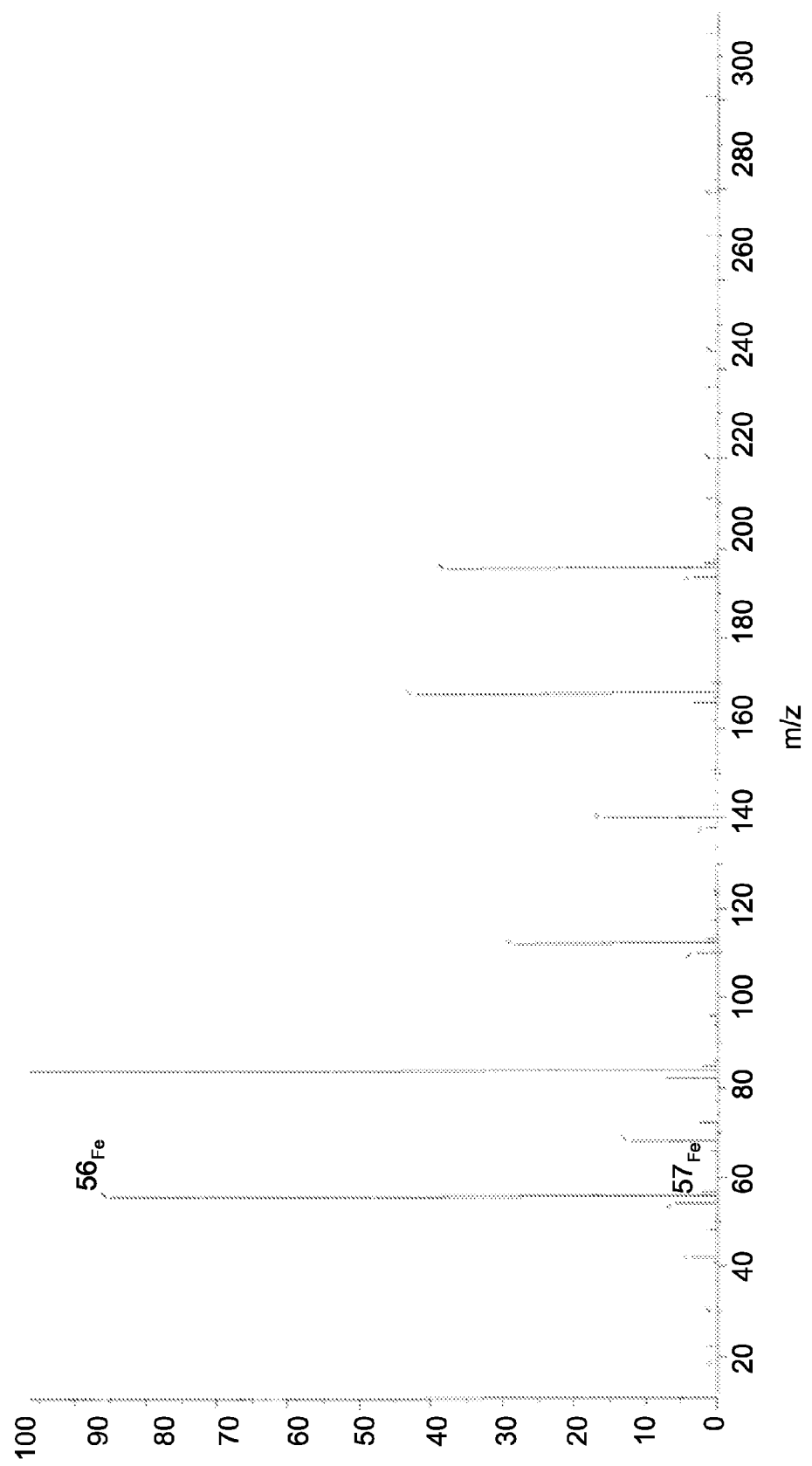
FIG. 2 shows mass spectrum of regular (non-isotope enriched) $Fe(CO)_5$.

FIG. 2 shows the mass spectrum of regular (non-isotope enriched) Fe(CO)$_5$. The peak 56 corresponds to natural Fe isotope. Peak 57 corresponds to $^{57}$Fe present in the regular Fe(CO)$_5$.

Figure 3:
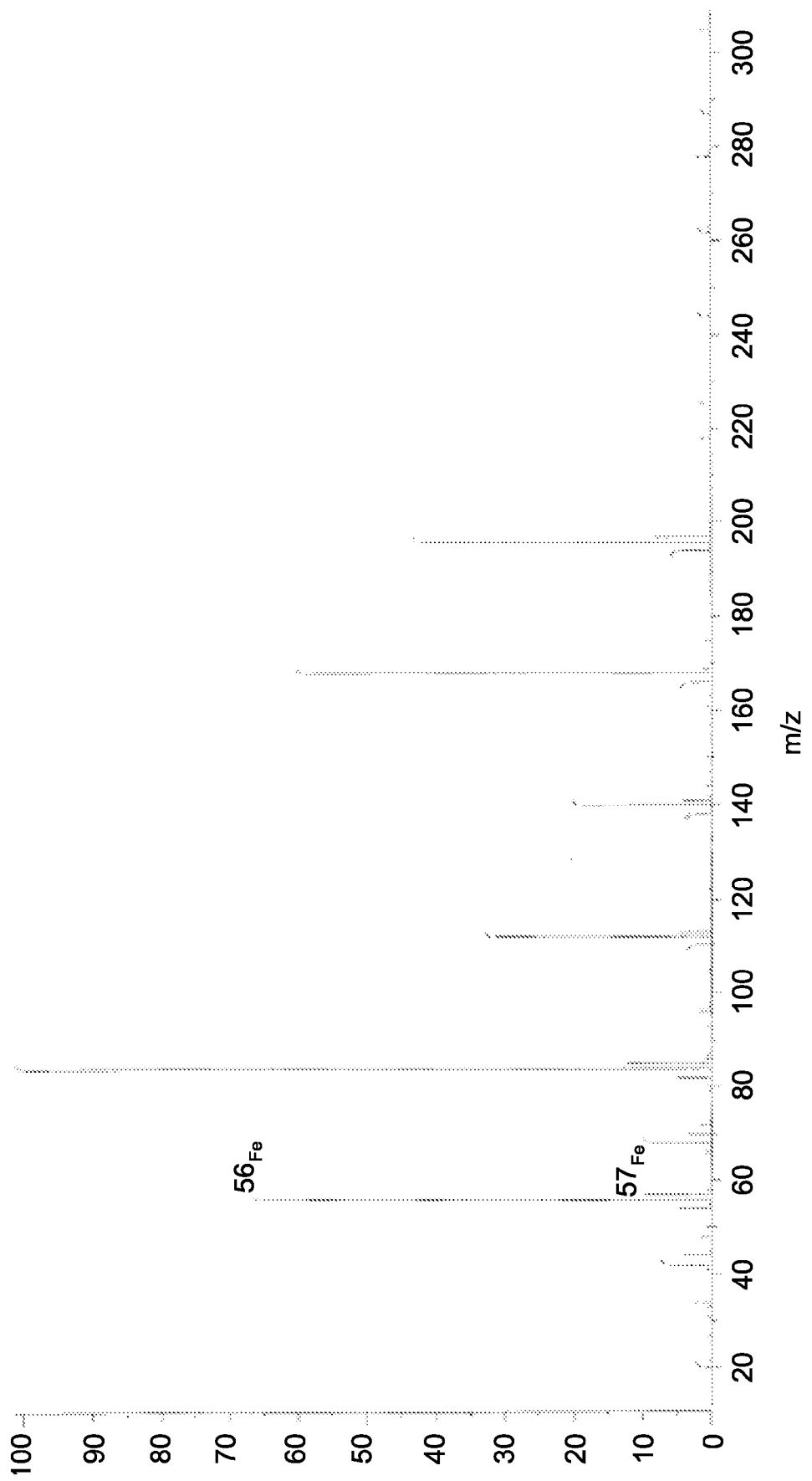
FIG. 3 shows mass spectrum of $^{57}Fe$-enriched $Fe(CO)_5$.

FIG. 3 shows the mass spectrum of $^{57}$Fe enriched Fe(CO)$_5$ ($^{57}$Fe(CO)$_5$). The peak 56 corresponds to natural Fe isotope. Peak 57 corresponds to $^{57}$Fe present in the $^{57}$Fe(CO)$_5$. The $^{57}$Fe peak intensity in FIG. 3 is higher than $^{57}$Fe peak intensity in FIG. 2. This clearly demonstrates the $^{57}$Fe enrichment in $^{57}$Fe(CO)$_5$ compared to regular Fe(CO)$_5$.

Example 2

Synthesis of Non-Radioactive $^{57}$Fe Enriched Superparamagnetic Iron Oxide (SPIO) Nanoparticle

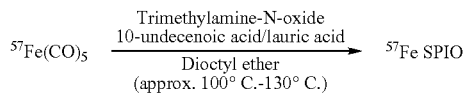

Trimethyl-N-oxide, 10-undecanoic acid, lauric acid and dioctyl ether were each individually dehydrated and deoxygenated. A mixture of trimethylamine-N-oxide (7.60 mmol), 10-undecenoic acid (4.56 mmol) and 7 ml of dioctyl ether or a mixture of trimethylamine-N-oxide (7.60 mmol), lauric acid (4.56 mmol) and 7 ml dioctyl ether were added under an inert atmosphere to a 50 ml two neck Schlenk flask. The flask was attached to a Schlenk vacuum-line, and a column-reflux condenser assembly was attached under a blanket of N$_2$. The mixture was homogenized witvigorous stirring and heating to about 100° C.

The reaction mixture was then kept at temperature in a range from about 100° C. to about 105° C. and was stirred slowly. To this was added about 1.52 mmol of non-radioactive isotopically enriched iron-57 carbonyl (Fe(CO)$_5$), resulting in instantaneous and aggressive reaction. Non-radioactive Iron-57 enriched carbonyl (Fe(CO)$_5$) addition was completed in less than a minute and the intense reaction subsided. The reaction mixture was then heated to a temperature in a range from about 120° C. to about 130° C. under N$_2$ and maintained at temperature for 1 hour with vigorous stirring.

About 0.76 mmol of non-radioactive isotopically enriched iron-57 carbonyl ($^{57}$Fe(CO)$_5$) was then added to the reaction mixture. The temperature of the reaction mixture was rapidly increased to about 300° C. to allow the reaction mixture to reflux. After 1 hour of refluxing and stirring at about 300° C., the color of the reaction mixture turned black. The reaction mixture was then cooled to room temperature, and an equal volume amount of isopropyl alcohol was added to the reaction mixture, yielding a black precipitate. The precipitate was separated by centrifuging and collected by magnetic decantation. Particles were readily dispersed in toluene and octane, forming homogeneous solutions. Crystal structure, composition, and particle size analysis of the powder were obtained by transmission electron microscopy (TEM) imaging, energy dispersive x-ray (EDX) elemental analysis, x-ray absorption spectroscopy (XAS), and selected area electron diffraction/ x-ray diffraction (SAED-XRD) crystal symmetry pattern indexing. The powder obtained was found to comprise monodisperse mixed non-radioactive isotopically enriched γ-iron-57 oxide/ferrite γ-(Fe$_2$O$_3$)$_{1-y}$(Fe$_3$O$_4$)$_y$ nanocrystals, each having a particle size of about 5 nm(±)0.5 nm. The y-value is generally about 0.4 to about 0.5.

Surface treatment of the non-radioactive traceable metal isotope enriched SPIO nanoparticles is required prior to mammalian injection. To treat the surface, one example treatment may be comprised of: adding tetrahydrofuran (10 mL) to a vial containing 3.25 mg Fe/mL 5 nm SPIO in tetrahydrofuran (4.0 mL, 13 mg Fe, 0.232 mmol), followed by 50% PEI silane in isopropyl alcohol (2.0 mL). The resulting cloudy solution was sonicated for 2 hours. Isopropanol (4.0 mL) was then added and sonicated for an additional 16 hours. Concentrated NH$_4$OH (1.0 mL, 14.8 mmol) was then added and stirred at room temperature for 4 hours. The solution was then diluted with H$_2$O (10 mL) and extracted with hexanes (3.times.10 mL) and ethyl acetate (3.times.10 mL). Any remaining organics in the aqueous layer were removed in vacuo. The resulting homogeneous aqueous solution was passed through a 200 nm syringe filter followed by a 100 nm syringe filter. The solution was then diluted with H$_2$O (10 mL total volume) and purified using a 100 kDa MW cutoff filter (2680.times.g until .about.3 mL of solution remained). The centrifuge filtration process was preferably carried out a total of six times. The final pH of the solution was adjusted to about 7.4 to about 7.7 using concentrated HCl as necessary. Treated in this way, the non-radioactive traceable metal isotope enriched SPIO nanoparticles may be used for mammalian injection.

Example 3

Method for Sample Collection

Non-radioactive isotope-enriched superparamagnetic iron oxide ($^{57}$Fe labeled SPIO, referred as $^{57}$FeSPIO) nanoparticles were injected into rats (female Lewis rats, ~200 g) and mice (female Swiss Webster mice, ~25 g), and blood clearance and tissue distribution were determined. Blood was collected either by catheterization of the tail vein or by terminal cardiac puncture of the rodents. Blood collection tubes were treated with anticoagulant (to achieve 10 U/mL heparin or 5 mM EDTA). Tubes for tissue collection were pre-weighed for determining the total organ weight after collection of sample.

Blood samples were collected from the rats and mice before injection of isotope-enriched superparamagnetic iron oxide ($^{57}$FeSPIO) agent. The animals were then injected with a known quantity (typically chosen to be between 1 to 5 mg Fe/kg body weight) of $^{57}$FeSPIO nanoparticles through the tail vein. Blood samples (~50 uL) were collected, with typical time points at 5 & 30 min, and 1, 2, 4, 8, 24 and 48 hours following injection. To collect plasma sample, the blood sample was immediately placed on ice and centrifuged cold (e.g., 300×g, 10 min, at 4° C.).

At the terminal time point, typically 1, 7 or 14 days post injection, blood samples were collected by cardiac puncture under deep anesthesia. The animal was euthanized and tissues of interest were collected, rinsed in saline and weighed.

Example 4

MR Imaging

In addition to the collection of blood, plasma and tissue samples described above, magnetic resonance (MR) images were also collected at time points of interest. Images were typically collected using T1, T2 and T2* weighted pulse sequences. Field strength of 1.5 Tesla; R1~10-20 mM-1 s−1. R2~40-60 mM-1 s$^{-1}$ were used (on a per iron atom basis). The MR data enabled comparison of the $^{57}$Fe labeled SPIO ($^{57}$FeSPIO) nanoparticle's biodistribution determined analytically with the tissue associated contrast enhancement in the various tissues.

Example 5

Method for Sample Digestion and Determination of Spike Recovery

The blood and tissue samples were stored at −20° or −80° C. prior to elemental analysis. The tissues samples were thawed and coarsely homogenized with a blade. The concentration of $^{57}$Fe and the ratio of $^{57}$Fe to $^{54}$Fe ratio were then determined.

Samples were accurately weighed, and added into Mars 5 microwave vessels. 2.5 ml of HNO$_3$, 1 ml of H$_2$O$_2$ and 1.5 ml H$_2$O were added to each microwave vessel. The samples were allowed to stand overnight to pre-digest. The samples were digested in a Mars 5 microwave digestion system. The vessels were allowed to cool. The solutions were quantitatively transferred to 50 mL disposable plastic centrifuge tubes and brought up to 20 gm. Similarly, blanks and spiked samples were prepared and analyzed. For the spiked samples, known amount of $^{57}$Fe was added to an aliquot of the biological specimen before the microwave digestion started and was prepared and analyzed in the same fashion as the samples. Spike recovery was then calculated according the following equation:

$$\text{Spike recovery} = \frac{^{57}\text{Fe in the spiked sample} - {}^{57}\text{Fe in the unspiked sample}}{^{57}\text{Fe that was added to the spiked sample (known)}} \times 100$$

The spike recovery was used as the quality assurance check to verify the accuracy of the analytical results. Spike recoveries typically ranged from 90-110%. This indicated that all $^{57}$Fe analyte has been fully digested and accounted for the analysis with good accuracy. The $^{57}$Fe enrichment in the digested samples was determined by elemental analysis using an Element 2 ICP-MS instrument as described below.

Example 6

Elemental Analysis: Solution Nebulization ICP-MS (Thermo Finnegan, Element 2)

All digested samples were diluted 40 times for ICP-MS analysis with the addition of 10 ppb $^{89}$Yttrium ($^{89}$Y) as an internal standard. The analyte concentrations were calculated by comparison with a known series of matrix matched external calibration standards (0-50 ppb), containing 10 ppb $^{89}$Y as internal standard. A 200 ppb Fe standard solution (with natural abundance) prepared from High Purity Standard (Charlston, S.C. 29423, USA) stock solution was analyzed to correct for the difference between the natural abundance and the measured ratio. The same solution was also analyzed after every 5 samples to check and correct for the drift of $^{57}$Fe/$^{54}$Fe ratio. All samples were analyzed on the following instrumentation, using the conditions outlined in Table 1:

TABLE 1

| Instrumental parameters for the ICP-MS analysis | | |
|---|---|---|
| Instrumentation | | |
| Element 2 | | |
| Elemental Scientific E2 Autosampler | | |
| Poly-nebulizer from Elemental Scientific (self aspirating) | | |
| Finnegan E2 torch with sapphire insert | | |
| Method Conditions | | |
| Pump Rate: self aspirating | | |
| Detector: SEM | | |
| Auto Masslock: On | Sample Uptake: 30 sec | |
| ICP RF Power: 1050 watts | Rinse Time: 15 sec | |
| Masses | Fe57 | Fe54 |
| Run | 3 | 3 |
| Pass | 3 | 3 |
| Resolution | Medium (4000) | Medium (4000) |

10 ppb of isotope $^{89}$Y was added to both the standards and all the samples. Isotope $^{89}$Y was used as internal standard where $^{57}$Fe and $^{54}$Fe intensities were normalized to $^{89}$Y to compensate for any instrument drift in a long run and also to correct for any potential matrix impact.

A schematic illustrating the data obtained by elemental analysis of digested tissues is shown in FIG. 1. A non-radioactive traceable iron isotope enriched SPIO nanoparticle ($^{57}$Fe$_{SPIO}$) may be employed by the present technique to determine $^{57}$Fe$_{SPIO}$ concentration in biological samples for characterization of biodistribution and clearance of the nanoparticle. As illustrated, there were 3 isotopic ratios of $^{57}$Fe to $^{54}$Fe that were relevant in this analysis. One of the three ratios was the ratio of non-radioactive traceable iron isotopes ($^{57}$Fe$_{SPIO}$ to $^{54}$Fe$_{SPIO}$) in the superparamagnetic iron oxide ($^{57}Fe_{SPIO}$) nanoparticle 10 (generally represented by 'S'), as shown in FIG. 1. As seen in FIG. 1 a nanoparticle 10 comprises $^{57}Fe$ and other isotopes of Iron (for example $^{56}Fe$, $^{54}Fe$, $^{58}Fe$ or combinations thereof). The ratio of non-radioactive traceable iron isotopes ($^{57}Fe$ to $^{54}Fe$) was measured by elemental analysis for each of the $^{57}Fe_{SPIO}$. It should be noted that, the ratio S is generally known for a given non-radioactive traceable $^{57}Fe$ enriched superparamagnetic iron oxide ($^{57}Fe_{SPIO}$) nanoparticle preparation. Second of the three ratios is the ratio of natural abundance (endogenous Iron content of the tissue) of the above-mentioned isotopes ($^{57}Fe_{natural}$ to $^{54}Fe_{natural}$), in a tissue sample 12 (generally represented by 'N'). As will be appreciated by those skilled in the art, the value of N is generally a known quantity. The third ratio is the ratio of the non-radioactive traceable iron isotopes ($^{57}Fe_{sample}$ to $^{54}Fe_{sample}$) (generally represented by 'M') measured in a given tissue sample 14 by elemental analysis upon the tissue sample being injected with $^{57}Fe_{SPIO}$. The nanoparticle enriched tissue sample 14 contains $^{57}Fe$ enriched SPIO nanoparticles as well as the endogenous Iron isotopes already present in the tissue sample. Note that a similar analysis could be implemented using total iron or another iron isotope in place of $^{54}Fe$ in these ratios, and likewise other isotopes could be used for labeling by enrichment.

M depends on the both on the endogenous iron content of the tissue and on the concentration of $^{57}Fe_{SPIO}$ in the tissue:

$$M = \frac{^{57}Fe_{sample}}{^{54}Fe_{sample}}$$
$$= \frac{^{57}Fe_{SPIO} + ^{57}Fe_{natural}}{^{54}Fe_{SPIO} + ^{54}Fe_{natural}}$$

The concentration of $^{57}Fe$ in the sample attributable to $^{57}Fe_{SPIO}$ can be calculated as:

$$^{57}Fe_{SPIO} = \frac{^{57}Fe_{sample}/M - ^{57}Fe_{sample}/N}{1/S - 1/N}$$

Knowing the $^{57}Fe$ enrichment in the $^{57}Fe_{SPIO}$ preparation (e.g., $^{57}Fe_{SPIO}$: SPIO (SPIO with natural Fe isotope), determined for each core prep), the total iron concentration in the tissue attributable to $^{57}Fe_{SPIO}$ is given by:

SPIO=$^{57}Fe_{SPIO}$/Enrichment

TABLE 2

Natural abundance of common iron isotopes.

| Isotope | Natural Abundance |
|---|---|
| $^{54}Fe$ | 5.8% |
| $^{56}Fe$ | 91.7% |
| $^{57}Fe$ | 2.2% |
| $^{58}Fe$ | 0.3% |

Natural abundance of common iron isotopes are given in Table 2. The iron concentration in tissue attributable to SPIO and $^{57}FeSPIO$ may be used to calculate percentage of injected dose (% ID or % ID/g) statistics by dividing by the total iron dose of SPIO.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A nanoparticle, comprising:
   at least one inorganic core; and
   at least one coating substantially covering the inorganic core, wherein the inorganic core comprises at least one enriched non-radioactive traceable metal isotope wherein the at least one of the enriched non-radioactive traceable element comprises $^{57}Fe$.

2. The nanoparticle of claim 1, wherein the nanoparticle has a diameter in a range of from about 1 nm to about 1000 nm.

3. The nanoparticle of claim 1, wherein the nanoparticle has a diameter in a range of from about 1 nm to about 10 nm.

4. The nanoparticle of claim 1, wherein the enriched non-radioactive traceable metal isotope is present in a range of from about 1% to about 99%.

5. The nanoparticle of claim 1, wherein the inorganic core further comprises at least one natural metal isotope of a metal selected from a group consisting of iron, manganese, copper, titanium, cadmium, cobalt, nickel, chromium, gadolinium, yttrium, zinc, molybdenum, vanadium, and derivatives thereof.

6. The nanoparticle of claim 1, wherein the enriched non-radioactive traceable metal isotope further comprises at least one isotope of a metal selected from a group consisting of iron, manganese, copper, titanium, cadmium, cobalt, nickel, chromium, gadolinium, yttrium, zinc, molybdenum, vanadium, and combinations thereof.

7. The nanoparticle of claim 1, wherein the enriched non-radioactive traceable metal isotope further comprises at least one Fe isotope selected from a group consisting of $^{54}Fe$, and $^{58}Fe$.

8. The nanoparticle of claim 1, wherein the coating comprises a biocompatible material.

9. The nanoparticle of claim 8, wherein the biocompatible material comprises an organo-silane compound.

10. The nanoparticle of claim 9, wherein the organo-silane compound is further derivatized with polyethylene glycol, polyethylene imine, dextran, or combinations thereof.

11. A superparamagnetic nanoparticle comprising:
   at least one superparamagnetic iron oxide core, and at least one coating substantially covering the superparamagnetic iron oxide core, wherein the superparamagnetic iron oxide core comprises at least one enriched non-radioactive traceable metal isotope wherein the at least one of the enriched non-radioactive traceable element comprises $^{57}Fe$; and
   the superparamagnetic nanoparticle has a diameter in a range of from about 1 nm to about 1000 nm.

12. The superparamagnetic nanoparticle of claim 11, wherein the enriched non-radioactive traceable metal isotope further comprises at least one Fe isotope selected from a group consisting of $^{54}Fe$, and $^{58}Fe$.

13. The superparamagnetic nanoparticle of claim 11, wherein the superparamagnetic nanoparticle has a diameter in a range of from about 1 nm to about 10 nm.

14. The superparamagnetic nanoparticle of claim 11, wherein the coating comprises a biocompatible organo-silane compound.

15. A method of forming a plurality of nanoparticles, wherein the method comprises
(a) combining a non-polar aprotic organic solvent, an oxidant, and a first surfactant, to form a first solution;
(b) adding at least one organometallic compound to the first solution, to form a second solution, wherein the at least one organometallic compound comprises at least one enriched non-radioactive traceable metal isotope and at least one ligand wherein the at least one of the enriched non-radioactive traceable element comprises $^{57}$Fe; and
(c) heating the second solution to a temperature in a range of from about 30° C. to about 400° C., to form the plurality of nanoparticles, wherein the plurality of nanoparticles comprise at least one inorganic core and at least one coating substantially covering the inorganic core, wherein the inorganic core comprises at least one enriched non-radioactive traceable metal isotope.

16. The method of claim 15, wherein the organometallic compound further comprises at least one enriched non-radioactive traceable metal isotope selected from a group consisting of $^{54}$Fe, and $^{58}$Fe.

17. A method for determining a distribution of nanoparticles in a biological material comprising the steps of:
(a) introducing the nanoparticles into the biological material,
wherein the nanoparticles comprise at least one inorganic core, wherein the inorganic core comprises at least two metal isotopes in a predetermined ratio, wherein at least one metal isotope is enriched non-radioactive traceable metal isotope wherein the at least one of the enriched non-radioactive traceable element comprises $^{57}$Fe; and
(b) determining the distribution of the nanoparticles in the biological material based on the predetermined ratio of the metal isotopes.

18. The method of claim 17, wherein the enriched non-radioactive traceable metal isotope further comprises at least one isotope of a metal selected from a group consisting of iron, manganese, copper, titanium, cadmium, cobalt, nickel, chromium, gadolinium, yttrium, zinc, molybdenum, vanadium, and combinations thereof.

19. The method of claim 17, wherein the inorganic core further comprises $^{54}$Fe or $^{58}$Fe.

20. The method of claim 17, wherein the nanoparticle has a diameter in a range of from about 1 nm to 1000 nm.

21. The nanoparticle of claim 17, wherein the nanoparticle has a diameter in a range of from about 1 nm to about 10 nm.

22. The method of claim 17, wherein the enriched non-radioactive traceable metal isotope is present in a range of from about 1% to about 99%.

* * * * *